(12) United States Patent
Wang et al.

(10) Patent No.: US 6,579,436 B2
(45) Date of Patent: Jun. 17, 2003

(54) GAS SENSOR AND METHOD OF PRODUCING THE SAME

(75) Inventors: Da Yu Wang, Troy, MI (US); Paul C. Kikuchi, Fenton, MI (US); Walter T Symons, Grand Blanc, MI (US); Kaius K. Polikarpus, Grand Blanc, MI (US); Larry M. Oberdier, Royal Oak, MI (US)

(73) Assignee: Delphi Technologies, Inc., Troy, MI (US)

( * ) Notice: Subject to any disclaimer, the term of this patent is extended or adjusted under 35 U.S.C. 154(b) by 227 days.

(21) Appl. No.: 09/740,354

(22) Filed: Dec. 18, 2000

(65) Prior Publication Data

US 2002/0108855 A1 Aug. 15, 2002

(51) Int. Cl.$^7$ ............................................. G01N 27/407
(52) U.S. Cl. ..................... 204/425; 204/426; 204/427; 204/429; 427/58
(58) Field of Search ................................. 204/421–429

(56) References Cited

U.S. PATENT DOCUMENTS

| | | | |
|---|---|---|---|
| 4,158,166 A | | 6/1979 | Isenberg |
| 4,798,693 A | * | 1/1989 | Mase et al. |
| 4,861,456 A | * | 8/1989 | Mase et al. |
| 4,880,519 A | * | 11/1989 | Wang et al. |
| 5,236,569 A | * | 8/1993 | Murase et al. |
| 5,762,737 A | | 6/1998 | Bloink et al. |
| 6,270,639 B1 | * | 8/2001 | Lenfers et al. |
| 6,306,271 B1 | * | 10/2001 | Kato et al. |

OTHER PUBLICATIONS

Electrochemical Methods, p. 152–157, Allen J. Bard and Larry R. Faulkner, John Wiley and Sons, 1980.

* cited by examiner

*Primary Examiner*—T. Tung
(74) *Attorney, Agent, or Firm*—Vincent A. Cichosz

(57) ABSTRACT

A gas sensor, comprising an oxygen pump cell with a first pump electrode and a second pump electrode disposed on opposite sides of a first solid electrolyte layer and a second pump electrode. The sensor also comprises an emf cell with an emf electrode and a reference gas electrode disposed on opposite sides of a second solid electrolyte layer. The emf electrode is disposed in fluid communication to the second pump electrode. A via hole is disposed through the first solid electrolyte layer, such that the first pump electrode is in fluid communication with the second pump electrode. A protective insulating layer, having a passage for gas to be sensed, is disposed in contact with the first pump electrode. A first insulating layer, having a conduit, is disposed in contact with the emf electrode. A second insulating layer, having an air channel, is disposed in contact with the reference gas electrode. A heater is disposed in thermal communication with the emf cell. At least four electrical leads are in electrical communication with the sensor. A method of producing a gas sensor is disclosed.

14 Claims, 6 Drawing Sheets

GAS SENSOR AND METHOD OF PRODUCING THE SAME

TECHNICAL FIELD

The present invention relates to gas sensors, particularly to the leads connecting to the sensor.

BACKGROUND OF THE INVENTION

Exhaust sensors are used in a variety of applications that require qualitative and quantitative analysis of gases. For example, exhaust sensors have been used for many years in automotive vehicles to sense the presence of exhaust gases. In automotive applications, the direct relationship between various exhaust gas concentrations and the air-to-fuel (A/F) ratios of the fuel mixture supplied to the engine allows the sensor to provide concentration measurements for determination of optimum combustion conditions, maximization of fuel economy, and the management of exhaust emissions. The management of exhaust emissions has become increasingly important because of the increased use of automobile engines.

One method of sensing exhaust gas uses electrochemistry. With an electrochemical method, there are two basic principles involved in gas sensing: the Nernst principle and the polarographic principle. Typically, an exhaust gas sensor utilizing an electrochemical method comprises an electrochemical pump cell and an electrochemical motive force cell.

With the Nernst principle, chemical energy is converted into electromotive force ("emf"). A gas sensor based upon this principle typically consists of an ionically conductive solid electrolyte material, a porous electrode with a porous protective overcoat exposed to exhaust gases ("sensing electrode"), and a porous electrode exposed to a known gas's partial pressure ("reference gas electrode"). Sensors typically used in automotive applications use a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas With the polarographic principle, the sensors utilize electrolysis whereby ions are sensed through a diffusion limiting current for aqueous electrolyte systems. The same approach can be applied to solid electrolyte systems for sensing gas species and for sensing of wide range air-to-fuel ratio of combustion exhaust gas systems. Generally, a sensor employing the polarographic principle is composed of a pair of current pumping electrodes where both are in contact with an oxide conductive solid electrolyte and one electrode is in contact with a gas diffusion limiting medium. The gas diffusion limiting means in conjunction with the pump electrodes create a limiting current which is linearly proportional to the measured gas concentration in the sample.

By combining the cell using a polarographic method ("pump cell") and the cell using emf into one sensor, the sensor can be manufactured economically. However, a sensor of this type has a limited range of the air-to-fuel ratios covered as it is limited by the IR drop polarization of the electrolyte and the electrode potentials. The IR polarization is associated with the voltage gradient that is necessary, to drive the charged ions through the cell electrolyte, and the electrode potential to drive ions and electrons through the electrode and other conductive material. Typically, complex electronic circuits have been used to overcome the difficulties caused by the IR drop polarization of the electrolyte and the electrode potentials.

A known type of exhaust sensor includes a flat plate sensor formed of various layers of ceramic and electrolyte materials laminated and sintered together with electrical circuit and sensor traces placed between the layers in a known manner. Within the sensor, a flat plate sensing element is employed. This sensing element can be both difficult and expensive to package within the body of the exhaust sensor since it generally has one dimension that is very thin and is usually made of brittle materials. Consequently, great care and time consuming effort must be taken to prevent the flat plate sensing element from being damaged by exhaust, heat, impact, vibration, the environment, etc. This is particularly problematic since most materials conventionally used as sensing element supports, glass and ceramics for example, cannot withstand much bending. After the sensor is formed, exhaust gas can be sensed. With the use of ceramic materials, thermal shock resistance is a primary concern. This has an effect of influencing sensor manufacture because of the precautions taken to preserve during the sensor's lifetime the fragile ceramic materials, i.e., to prevent cracking from thermal shocks, and the sensor's electronics for heating control and sensing.

To prevent poisoning of exhaust sensor electrodes, exhaust gas poison resistance is maintained to protect the sensor during its lifetime. Sensor electrodes can be poisoned in various ways. For example, engine exhaust contain compounds such as silica, lead and other compounds that can poison the sensor. When the engine is in combustion mode, the sensor contacts exhaust. Particles from the engine parts or from other sources such as inferior fuel containing silica, lead and other compounds pass through the pores of the sensor's protective layer and adhere to the surface of the sensor's ceramics or adsorb on the surface of the electrode. This process can lead to the poisoning of the sensor causing deterioration of the sensor output and its response properties. To prevent poisoning, sensors have each electrode with poison protection. Sensor construction is more complex and difficult if each electrode maintains its own poison resistance. Accordingly, there remains a need in the art for a sensor having electrodes that share the same poison protection to render sensor fabrication simpler and more economic.

SUMMARY OF THE INVENTION

The deficiencies of the above-discussed prior art are overcome or alleviated by the gas sensor and method of producing the same.

A gas sensor, comprising an oxygen pump cell with a first pump electrode and a second pump electrode disposed on opposite sides of a first solid electrolyte layer and a second pump electrode. The sensor also comprises an emf cell with an emf electrode and a reference gas electrode disposed on opposite sides of a second solid electrolyte layer. The emf electrode is disposed in fluid communication to the second pump electrode. A via hole is disposed through the first solid electrolyte layer, such that the first pump electrode is in fluid communication with the second pump electrode. A protective insulating layer, having a passage for gas to be sensed, is disposed in contact with the first pump electrode. A first insulating layer, having a conduit, is disposed in contact with the emf electrode. A second insulating layer, having an air channel, is disposed in contact with the reference gas electrode. A heater is disposed in thermal communication with the emf cell. At least four electrical leads are in electrical communication with the sensor.

A method of producing a gas sensor, comprising providing an oxygen pump cell having a first pump electrode and a second pump electrode disposed on opposite sides of a first solid electrolyte layer. Also comprising disposing an emf cell having an emf electrode and a reference gas electrode disposed on opposite sides of a second solid electrolyte layer, wherein said emf electrode is in fluid communication to said second pump electrode. Disposing a protective insulating layer, having a passage for gas to be sensed, in contact with the first pump electrode. Positioning a first insulating layer, having a conduit, in contact with the emf electrode. Disposing a via hole through the first electrolyte layer such that the first pump electrode is in fluid communication with the second pump electrode. Disposing a second insulating layer, having an air channel, in contact with the emf cell. Positioning a heater in contact with the emf cell. Providing at least four electrical leads in electrical communication with the sensor.

The above discussed and other features and advantages of the present invention will be appreciated and understood by those skilled in the art from the following detailed description and drawings.

BRIEF DESCRIPTION OF THE DRAWINGS

The present invention will now be described, by way of example only, with reference to the accompanying drawings, which are meant to be exemplary, not limiting, and wherein like elements are numbered alike in several Figures, in which.

DETAILED DESCRIPTION OF INVENTION

The sensor design described herein utilizes both Nernst electrochemical motive force cells ("emf cells") and current-pumping type electrochemical cells ("pump cells"). Advantageously, the sensor has a reduced number of leads while remaining capable of covering a wide range of air to fuel ratios (e.g. an A/F ratio of about 8 to about 50). The sensor can have an alumina-zirconia-alumina-zirconia type composite structure that increases the mechanical and thermal shock resistance properties. Further, the sensor's electrodes share the same poison resistance which makes the sensor easier to fabricate and more economical.

Figure 1:
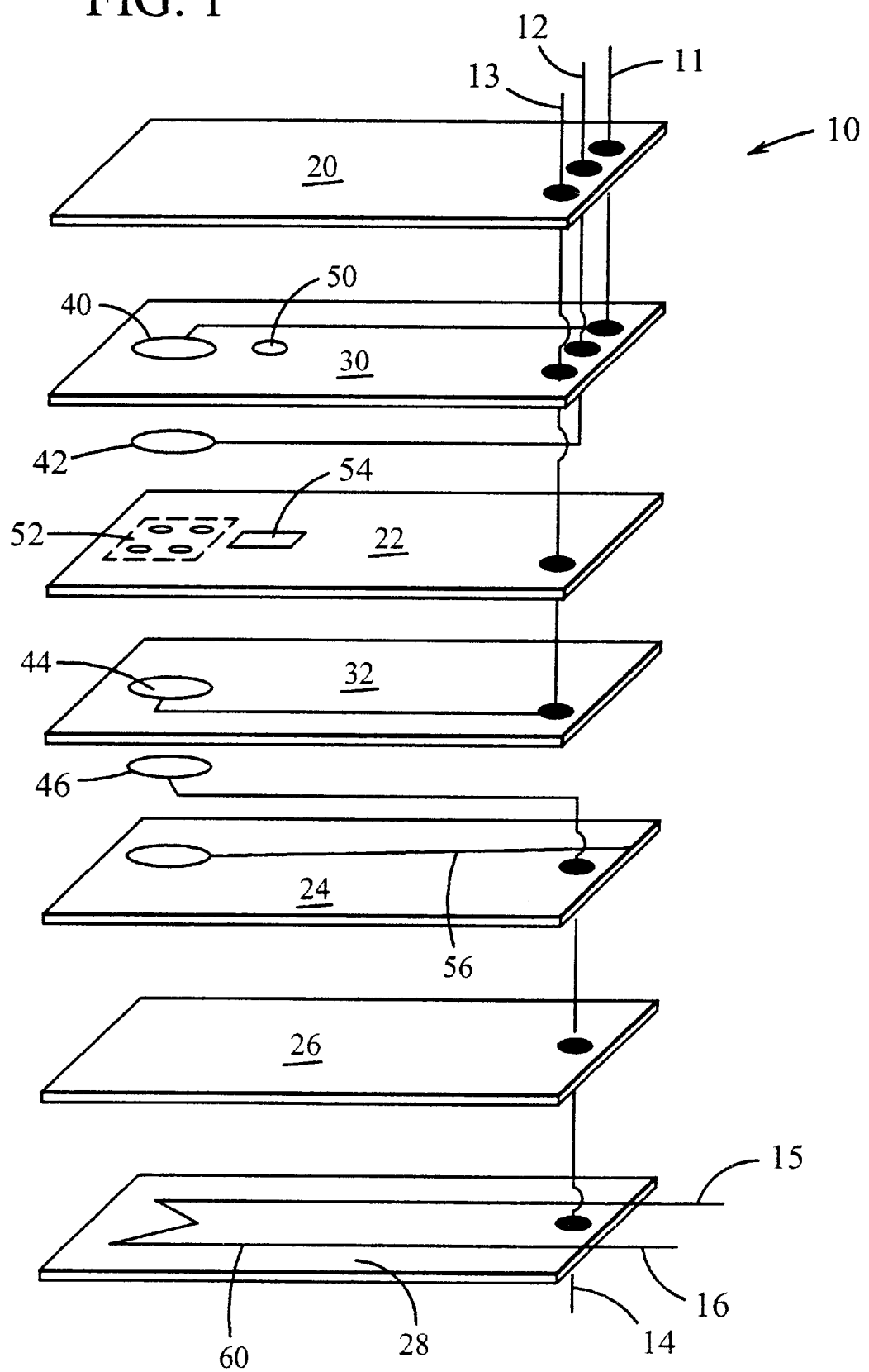
FIG. 1 is an exploded view of a sensor with a 6-lead structure.

Two electrochemical cells are used in one embodiment of the sensor 10 as shown in FIG. 1. The first is an oxygen pump cell with two pump electrodes 40 and 42 disposed in ionic communication with opposite sides of a first solid electrolyte layer 30. The second electrochemical cell is an emf cell with two electrodes 44 and 46 disposed in ionic communication with opposite sides of a second solid electrolyte layer 32 wherein one electrode 44 is an emf sensing electrode and the other electrode 46 is a reference gas electrode.

In a preferred arrangement, the emf cell and pump cell are arranged in an alumina-zirconia-alumina-zirconia layered structure about the electrodes to enhance the mechanical and thermal mechanical properties of the sensor element. Layers 30 and 32 are preferably a solid electrolyte that can comprise the entire layer or a portion thereof, can be any material that is capable of permitting the electrochemical transfer of oxygen ions while inhibiting the physical passage of exhaust gases, has an ionic/total conductivity ratio of approximately unity, and is compatible with the environment in which the gas sensor will be utilized (e.g., up to about 1,000° C.). Possible solid electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing. For example, the electrolyte can be alumina and yttrium stabilized zirconia. Typically, the solid electrolyte, which can be formed via many conventional processes (e.g., die pressing, roll compaction, stenciling and screen printing, tape casting techniques, and the like), has a thickness of up to about 500 microns, with a thickness of approximately 25 microns to about 500 microns preferred, and a thickness of about 50 microns to about 200 microns especially preferred.

It should be noted that, in some embodiments, a porous electrolyte may also be employed. The porous electrolyte should be capable of permitting the physical migration of exhaust gas and the electrochemical movement of oxygen ions, and should be compatible with the environment in which the gas sensor is utilized. Typically, porous electrolyte has a porosity of up to about 20%, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes that may be useful in the instant application. Possible porous electrolytes include those listed above for the solid electrolyte.

The various electrodes 40, 42, 44, and 46 are disposed on opposites sides of an in ionic contact with electrolyte layers 30 and 32. These electrodes can comprise any catalyst capable of ionizing oxygen, including, but not limited to, metals such as platinum, palladium, osmium, rhodium, iridium, gold, and ruthenium; metal oxides such as zirconia, yttria, ceria, calcia, alumina and the like; other materials, such as silicon, and the like; and mixtures and alloys comprising at least one of the foregoing catalysts. As with the electrolyte, the electrodes 40, 42, 44, and 46 can be formed using conventional techniques. Some possible techniques include sputtering, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. Electrode leads in the insulating and/or electrolyte layers are typically formed simultaneously with electrodes.

The electrodes 40, 42, and 44 are exposed to exhaust gas through a protective insulating layer 20. Individual poison protection for the pump electrodes 40 and 42, and the emf electrode 44 is achieved because of the presence of the protective insulating layer 20 and the design of the solid electrolyte layers 30 and 32 being separated by the insulating layers 22 and 24.

Insulating layers 20, 22, 24, 26, and 28, and any support layers, are typically capable of: providing structural integrity (e.g., effectively protecting various portions of the gas sensor from abrasion, vibration, and the like, and providing physical strength to the sensor); and physically separating and electrically isolating various components. The insulating layer(s), which can be formed using ceramic tape casting methods or other methods such as plasma spray deposition techniques, screen printing, stenciling and others conventionally used in the art, can each be up to about 200 microns thick, with a thickness of about 50 microns to about 200 microns preferred. Typically these insulating layers comprise a dielectric material such as spinel, alumina, magnesium aluminate, and the like, as well as combinations comprising at least one of the foregoing substances. Since the materials employed in the manufacture of gas sensor preferably comprise substantially similar coefficients of thermal expansion, shrinkage characteristics, and chemical compatibility in order to minimize, if not eliminate, delamination and other processing problems, the particular material, alloy or mixture chosen for the insulating layer is dependent upon the specific electrolyte employed.

It should be noted that the electrolyte layers 30 and 32, as well as protective insulating layers 20, 22, 24, 26, and 28, can comprise entire layer or any portion thereof, e.g., they can form the layer, be attached to the layer (protective material/electrolyte abutting dielectric material), or disposed an opening in the layer (protective material/electrolyte can be an insert in an opening in a dielectric material layer). The latter arrangement eliminates the use of excess electrolyte and protective material, and reduces the size of gas sensor by eliminating layers. Any shape can be used for the electrolyte and protective material, with the size and geometry of the various inserts, and therefore the corresponding openings, being dependent upon the desired size and geometry of the adjacent electrodes. It is preferred that the openings, inserts, and electrodes have a substantially similar geometry.

To pass gas onto the emf sensing electrode 44, gas passes through a via hole 50 on the first electrolyte layer 30. The sensing emf electrode 44 is in communication with a gas exposed to the pump electrode 42 through the insulating layer 22 having gas exchange holes 52 and/or a conduit 54, which is comprised of a porous channel for exhaust diffusion that is open to the emf electrode 44. Gas diffusion limiting means can be provided by the protective insulating layer 20, the via hole 50, the gas exchange holes 52, and the conduit 54, with the gas exchange holes 52 and the conduit 54 being more preferred. The reference gas electrode 46 is in communication with an air channel 56 connected with ambient air atmosphere. The air channel 56 can be disposed within or adjacent to the second insulating layer 24. Additionally, the reference gas electrode 46 can be exposed to oxygen by having oxygen pumped into the sensor by using an oxygen pump cell (can be pumped from first emf electrode to the reference gas electrode).

The air channel 56, the gas exchange holes (apertures) 52, and/or a conduit 54 are formed by depositing a fugitive material, e.g. carbon base material such as carbon black, such that upon processing the material burns out, and leaves a void. This fugitive material can be employed alone or in conjunction with an oxygen storage material. Possible oxygen storage materials include precious metals, alkaline materials, and the like, as well as combinations and alloys comprising at least one of the foregoing oxygen storage materials.

To maintain sensor 10 at proper operating temperature, a heater 60 is provided on an insulating layer 28 with an additional insulating layer 26 disposed between the heater 60 and the emf cell. Heater 60 can be any conventional heater capable of maintaining the sensor end at a sufficient temperature to facilitate the various electrochemical reactions therein. The heater 60, which is typically platinum, alumina, palladium, and the like, as well as mixtures and alloys comprising at least one of the foregoing metals, or any other conventional heater, is generally screen printed onto a substrate to a thickness of about 5 microns to about 50 microns.

Additional gas sensor components are conventional components in a gas sensor and can be employed. These additional components include, but not limited to, additional protective coatings (e.g., spinel, alumina, magnesium aluminate, and the like, as well as combinations comprising at least one of the foregoing coatings), lead gettering layer(s), ground plane(s), support layer(s), additional electrochemical cell(s), and the like. The leads, which supply current to the heater and electrodes, are typically formed on the same layer as the heater/electrode to which they are in electrical communication and extend from the heater/electrode to the terminal end of the gas sensor where they are in electrical communication with the corresponding via (not shown) and appropriate contact pad(s) (not shown).

Figure 2:
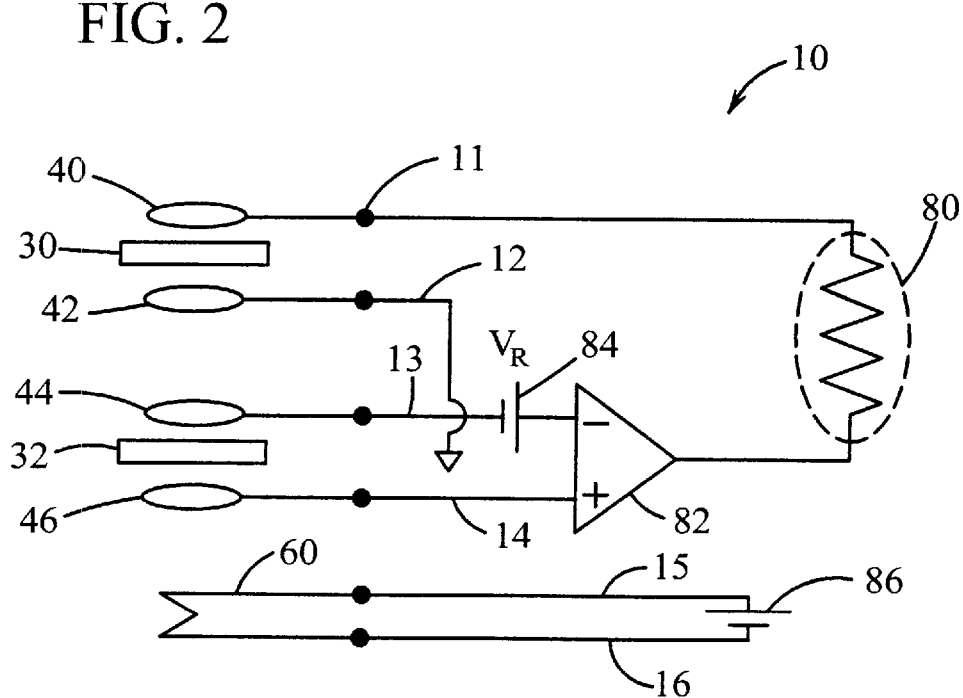
FIG. 2 is an electrical schematic of the sensor of FIG. 1.

Referring to FIG. 2, the sensor drive circuit for a 6-lead structure is depicted. Two leads 11 and 12 are for the oxygen pump cell and communicate with electrodes 40 and 42, respectively. Two leads 13 and 14 are for the emf cell and communicate with 44 and 46, respectively. External to the sensor electrode arrangement, lead 11 is in electrical communication with operational amplifier ("OP-amp") 82 with a region of resistance 80 between lead 11 and OP-amp 82. Leads 12 and 13 join externally to the sensor electrode arrangement and are in electrical communication with a power source $V_R$ 84. Power source 84 is thereafter connected to OP-amp 82. Lead 14 directly communicates with OP-amp 82. The remaining two leads 15 and 16 are for heater 60 and are attached to a power source 86.

Figure 4:
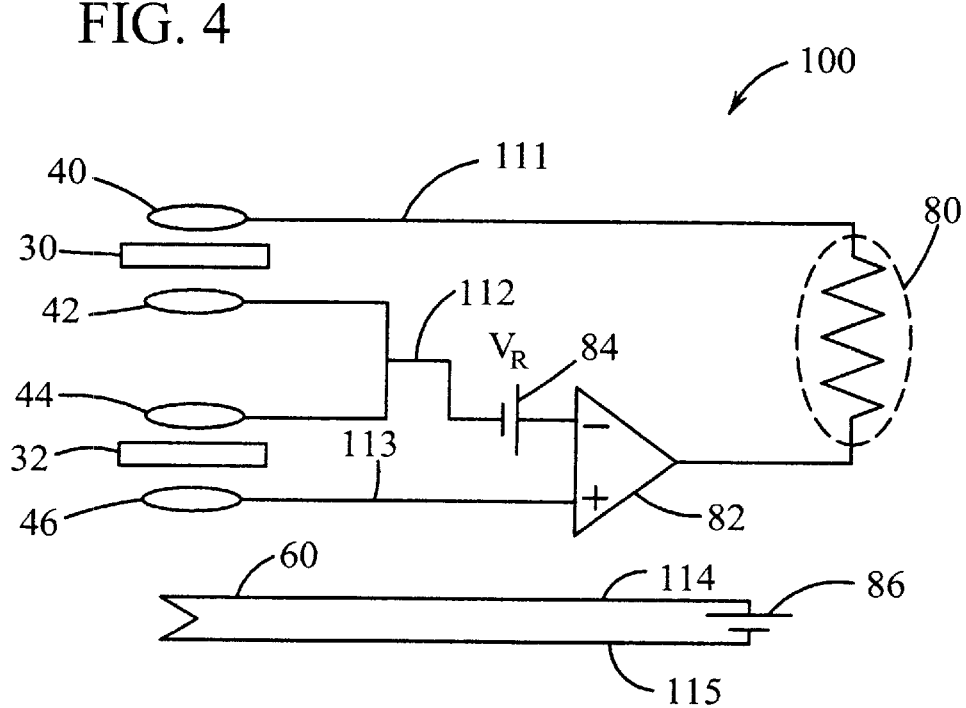
FIG. 4 is an electrical schematic of the sensor of FIG. 3.
Figure 3:
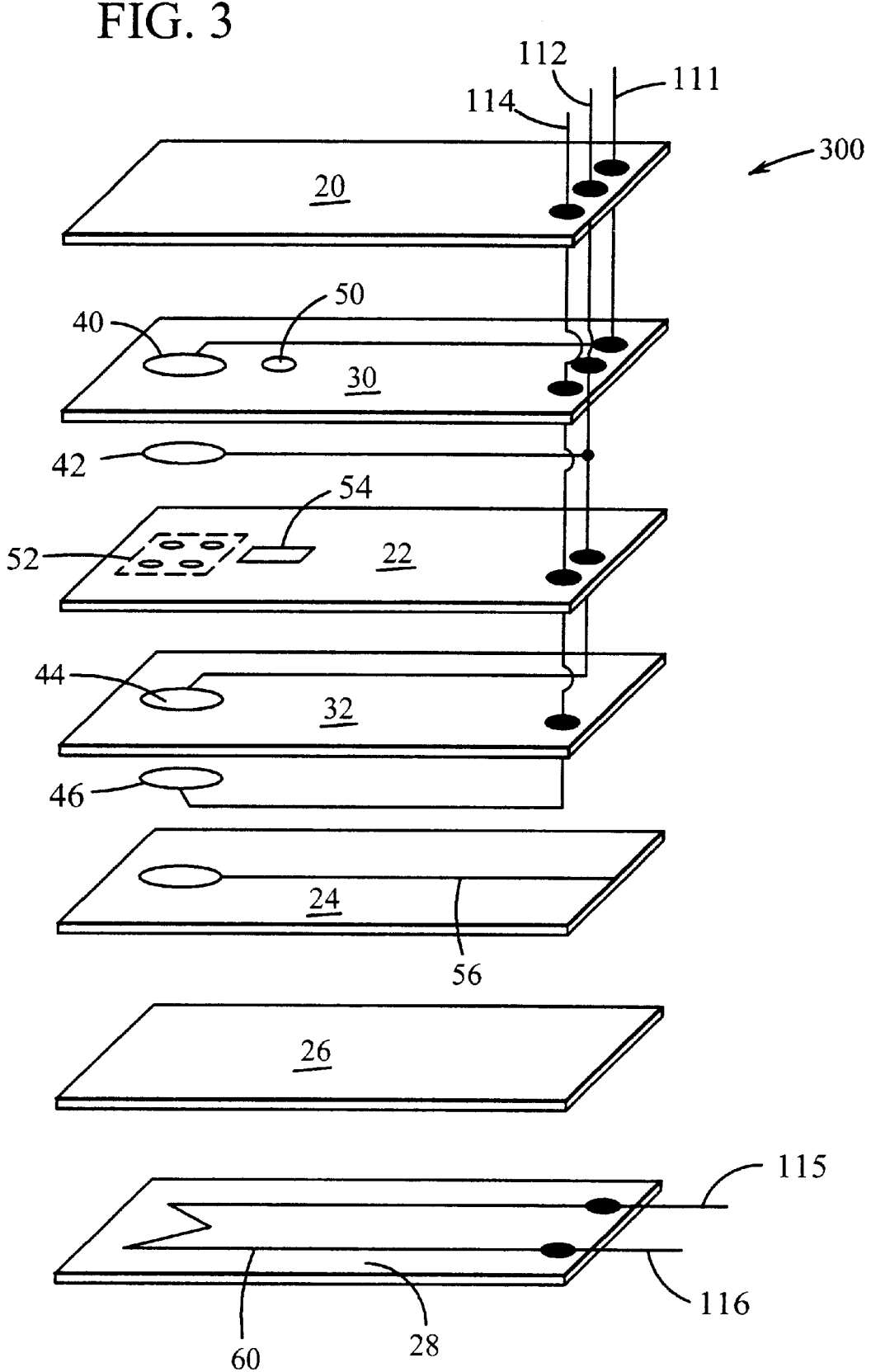
FIG. 3 is an exploded view of a sensor with a 5-lead structure.

In FIG. 3, sensor 100 is shown as a 5-lead device. One lead is eliminated from the 6-lead device by utilizing one lead 112 for both electrodes 42 and 44. Referring to the sensor drive circuit of FIG. 4, lead 112 is in electrical communication with OP-amp 82 and with a power source 84 between lead 112 and OP-amp 82. Pump electrode 40 is connected to lead 111, which is in electrical communication with OP-amp 82 with a region of resistance 80 between lead 111 and OP-amp 82. Reference gas electrode 46 is connected to lead 114, which directly communicates with OP-amp 82. Like the 6-lead device, the remaining two leads 115 and 116 are for heater 60 and are attached to power source 86.

Figure 5:
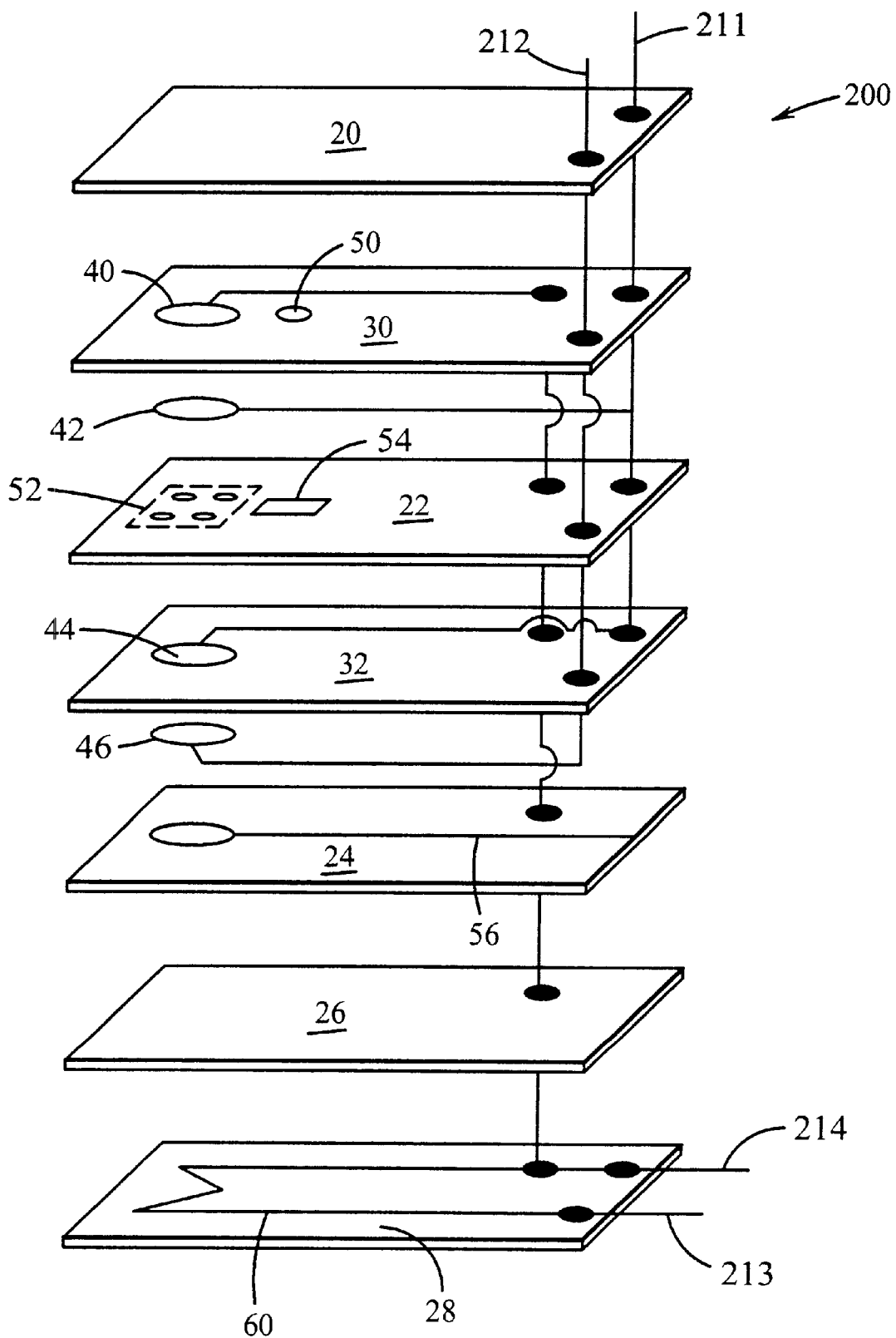
FIG. 5 is an exploded view of a sensor with a 4-lead structure.
Figure 6:
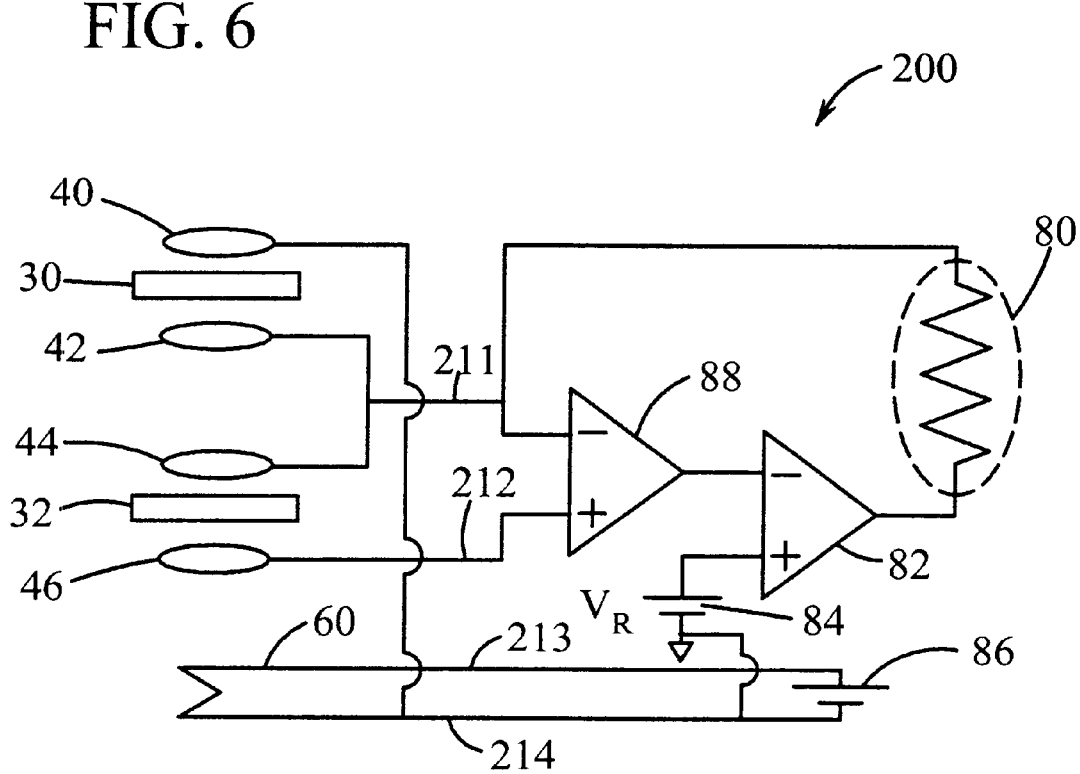
FIG. 6 is an electrical schematic of the sensor of FIG. 5.

Referring to FIG. 5 and sensor drive circuit of FIG. 6, sensor 200 is shown as a 4-lead device. The 4-lead device is achieved by having electrodes 42 and 44 share lead 211. Pump electrode 40 is connected to lead 214 (shown as the negative lead) of heater 60. Lead 211 connects to OP-amp 82 with region of resistance 80 disposed between lead 211 and OP-amp 82. Reference gas electrode 46 is connected to lead 212, which directly communicates with an instrument amplifier 88. One portion of instrument amplifier 88 is in communication with lead 211 and OP-amp 82 with resistance region 80 disposed between the two amplifiers. The other portion of instrument amplifier 88 directly communicates with OP-amp 82. As in the 5-lead embodiment, leads 213 and 214 of heater 60 are attached to power source 86.

Figure 8:
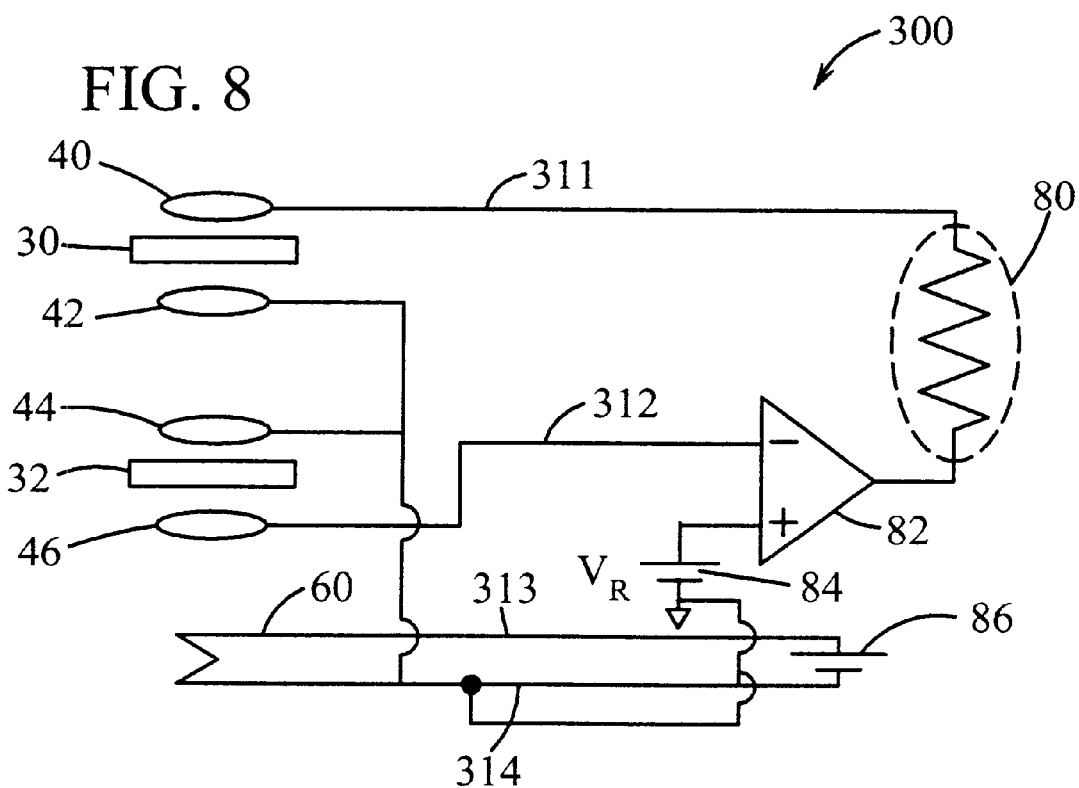
FIG. 8 is an electrical schematic of the sensor of FIG. 7.
Figure 7:
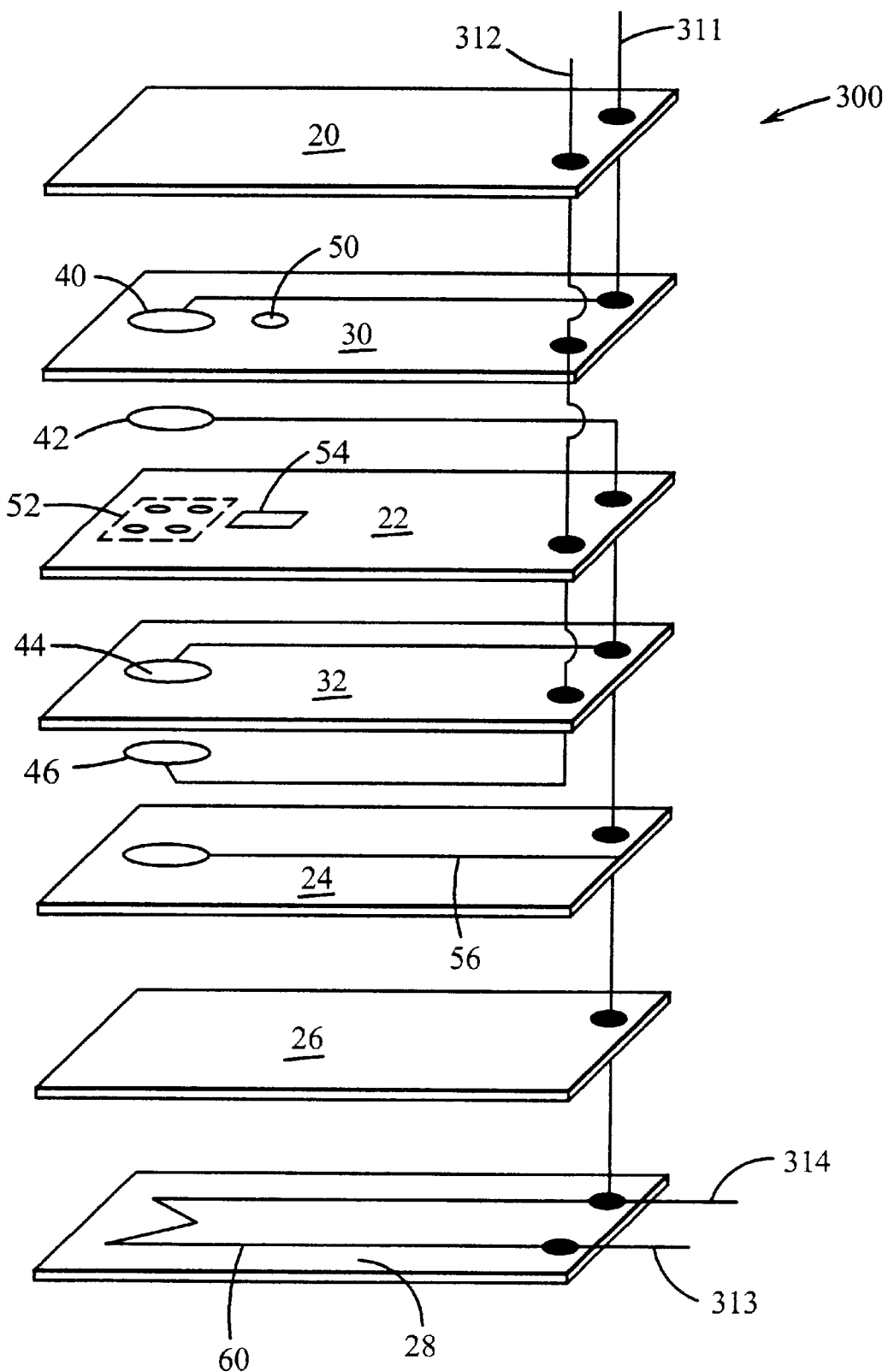
FIG. 7 is an exploded view of a sensor with an alternative 4-lead structure.

Sensor 300, having an alternative 4-lead device, is shown in FIG. 7 and the sensor drive circuit of FIG. 8. Therein, electrodes 42 and 44 are connected to share the lead 314 (shown as the negative lead) of heater 60. Pump electrode 40 is connected to lead 311, which communicates with OP-amp 82 with a region of resistance 80 between lead 311 and OP-amp 82. Lead 313 of heater 60 is attached to power source 86. Reference gas electrode 46 is connected to lead 312, which directly communicates with OP-amp 82. Further, OP-amp 82 is connected to power source 86 which is then connected to lead 314 of heater 60. With this arrangement, the connection of electrodes 42 and 44 to the negative lead of the heater 60 has a high conduction with a resistance less than about 0.1 ohm to eliminate emf drift caused by the IR drop of the current to the heater 60. Alternatively, pulses can be used to power the heater 60 with the emf measured between pulses.

With the embodiments described, sensors having improved performance and durability with an easier fabrication are obtained with a reduced number of leads to the gas sensor. Additionally, the composite structure of the sensor is designed such that the mechanical and thermal shock resistance properties are improved. These improvements are reached while using a single poison protection to protect the electrodes.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. A gas sensor, comprising:
    an oxygen pump cell having a first pump electrode and a second pump electrode disposed on opposite sides of a first solid electrolyte layer;
    an emf cell having an emf electrode and a reference gas electrode disposed on opposite sides of a second solid electrolyte layer, wherein said emf electrode is disposed in fluid communication to said second pump electrode;
    a protective insulating layer disposed in contact with said first pump electrode, said protective insulating layer provides a passage for gas to be sensed by said sensor;
    a first insulating layer disposed in contact with said emf electrode;
    a via hole disposed through said first solid electrolyte layer whereby said first pump electrode is in fluid communication wit said second pump electrode;
    a conduit disposed through said first insulating layer whereby said second pump electrode is in fluid communication with said emf electrode;
    a second insulating layer in contact with said reference gas electrode wherein an air channel is disposed;
    a heater disposed in thermal communication with said emf cell; and
    four electrical leads in electrical communication with said sensor, wherein said four electrical leads comprise a first lead in electrical communication with said first pump electrode, a second lead in electrical communication with said reference gas electrode, a third lead in electrical communication with said second pump electrode, said emf electrode, and said heater, and a fourth lead in electrical communication with said heater.

2. The gas sensor of claim 1, further comprising at least one insulating layer in contact with said heater.

3. The exhaust gas sensor of claim 1, further comprising gas exchange holes disposed on said first insulating layer adjacent to said conduit.

4. The exhaust gas sensor of claim 1, wherein said conduit is comprised of a porous material.

5. The exhaust gas sensor of claim 1, wherein said solid electrolyte layers are comprised of zirconia.

6. The exhaust gas sensor of claim 1, wherein said protective insulating layer and said insulating layers are comprised of alumina.

7. A gas sensor, comprising:
    an oxygen pump cell having a first pump electrode and a second pump electrode disposed on opposite sides of a first solid electrolyte layer;
    an emf cell having an emf electrode and a reference gas electrode disposed on opposite sides of a second solid electrolyte layer, wherein said emf electrode is disposed in fluid communication to said second pump electrode;
    a protective insulating layer disposed in contact with said first pump electrode, said protective insulating layer provides a passage for gas to be sensed by said sensor;
    a first insulating layer disposed in contact with said emf electrode;
    a via hole disposed through said first solid electrolyte layer whereby said first pump electrode is in fluid communication with said second pump electrode;
    a conduit disposed through said first insulating layer whereby said second pump electrode is in fluid communication with said emf electrode;
    a second insulating layer in contact with said reference gas electrode wherein an air channel is disposed;
    a heater disposed in thermal communication with said emf cell; and
    four electrical leads in electrical communication with said sensor, wherein said four electrical leads comprising a first lead in electrical communication with said second pump electrode and said emf electrode, a second lead in electrical communication with said reference gas electrode and a third lead in electrical communication with said first pump electrode and said heater, and a fourth lead in electrical communication with said heater.

8. A method of producing a gas sensor, comprising:
    providing an oxygen pump cell having a first pump electrode and a second pump electrode disposed on opposite sides of a first solid electrolyte layer;

disposing an emf cell having an emf electrode and a reference gas electrode disposed on opposite sides of a second solid electrolyte layer, wherein said emf electrode is in fluid communication to said second pump electrode;

disposing a protective insulating layer in contact with said first pump electrode, said protective insulating layer providing a passage for gas to be sensed by said sensor;

positioning a first insulating layer in contact with said emf electrode;

disposing a via hole though said first electrolyte layer whereby said first pump electrode is in fluid communication with said second pump electrode;

disposing a conduit through said first insulating layer providing a fluid communication between said second pump electrode and said emf electrode;

positioning a second insulating layer in contact with said emf cell, said second insulating layer providing an air channel;

positioning a heater in contact with said emf cell; and providing four electrical leads in electrical communication with said sensor by providing a first lead in electrical communication with said second pump electrode and said emf electrode, a second lead in electrical communication with said reference gas electrode, and a third lead in electrical communication with said first pump electrode and said heater, and a fourth lead in electrical communication with said heater.

9. The method of claim 8, wherein said solid electrolyte layers are composed of zirconia.

10. The method of claim 8, wherein said protective insulating layer and said insulating layers are composed of alumina.

11. The method of claim 8, further comprising disposing gas exchange holes on said first insulating layer adjacent to said conduit.

12. The method of claim 8, further comprising disposing at least one insulating layer in contact with said heater.

13. The method of claim 8, wherein said conduit is comprised of a porous material.

14. A method of producing a gas sensor, comprising:

providing an oxygen pump cell having a first pump electrode and a second pump electrode disposed on opposite sides of a first solid electrolyte layer;

disposing an cuff cell having an emf electrode and a reference gas electrode disposed on opposite sides of a second solid electrolyte layer, wherein said emf electrode is in fluid communication to said second pump electrode;

disposing a protective insulating layer in contact with said first pump electrode, said protective insulating layer providing a passage for gas to be sensed by said sensor;

positioning a first insulating layer in contact with said emf electrode;

disposing a via hole through said first electrolyte layer whereby said first pump electrode is in fluid communication with said second pump electrode;

disposing a conduit through said first insulating layer providing a fluid communication between said second pump electrode and said emf electrode;

positioning a second insulating layer in contact with said cuff cell, said second insulating layer providing an air channel;

positioning a heater in contact with said emf cell; and providing four electrical leads in electrical communication with said sensor, by providing a first lead in electrical communication with said first pump electrode, a second lead in electrical communication with said reference gas electrode, a third lead in electrical communication with said second pump electrode, said emf electrode, and said heater, and a fourth lead in electrical communication with said heater.

* * * * *